United States Patent [19]

Reiff et al.

[11] 4,118,411

[45] Oct. 3, 1978

[54] LOW-TEMPERATURE STORAGE STABLE LIQUID DIPHENYLMETHANE DIISOCYANATES

[75] Inventors: Helmut F. Reiff; Richard S. Pantone, both of New Martinsville, W. Va.

[73] Assignee: Mobay Chemical Corporation, Pittsburgh, Pa.

[21] Appl. No.: 766,997

[22] Filed: Feb. 9, 1977

[51] Int. Cl.$^2$ .......................................... C07C 119/048
[52] U.S. Cl. ....................... 260/453 SP; 260/453 AM
[58] Field of Search .................. 260/453 SP, 453 AM

[56] References Cited

U.S. PATENT DOCUMENTS

| 3,362,979 | 1/1968 | Bentley | 260/453 AM |
| 3,394,165 | 7/1968 | McClellan et al. | 260/453 SP |
| 3,644,457 | 2/1972 | Konig et al. | 260/453 SP |
| 3,883,571 | 5/1975 | Allport et al. | 260/453 AM |

Primary Examiner—Dolph H. Torrence
Attorney, Agent, or Firm—Gene Harsh; Joseph C. Gil; R. Brent Olson

[57] ABSTRACT

The instant invention is directed to novel low temperature, storage stable liquid diphenylmethane diisocyanates and to the method of their preparation. The diisocyanates of the instant invention are produced by reacting diphenylmethane diisocyanates having a specified 2,4'-isomer content with propylene glycol or poly-1,2-propylene ether glycols. It has been surprisingly found that the products of the instant invention are both stable and liquid at −5° C for at least 48 hours. In fact, in many instances, the products of the instant invention show no tendency to crystallize even when stored at −22° C for weeks.

22 Claims, No Drawings

LOW-TEMPERATURE STORAGE STABLE LIQUID DIPHENYLMETHANE DIISOCYANATES

BACKGROUND OF THE INVENTION

It is well known that diisocyanates which are liquid at room temperature (i.e., about 25° C.) have numerous advantages over solid diisocyanates because they are easier to mix and work with. However, diisocyanates which are liquid at room temperature and which are used on a large technical scale, such as toluene diisocyanate or hexamethylene diisocyanate, are as a rule physiologically harmful due to their high vapor pressure and therefore can only be used if certain safety precautions are taken. For this reason, various attempts have been made, either to start with diisocyanates that are normally liquid at room temperature and to reduce their physiological effects by certain procedures or to start with diisocyanates that are solid at room temperature and to convert these into liquid form. In both cases, however, one usually obtains either isocyanates of higher valency, i.e., tri- or polyisocyanates or higher molecular weight diisocyanates or a combination of these effects.

The most important diisocyanates which are solid at room temperature and which are readily available on a large commercial scale are 4,4'-diphenylmethane diisocyanate and the 2,4'-isomer thereof which melt at 39° C. and 34.5° C. respectively. Attempts have already been made to liquify both the 4,4'-diphenylmethane diisocyanate and a mixture of the 4,4'-diphenylmethane diisocyanate and a small amount of the 2,4'-isomer. Thus, for example, in U.S. Pat. No. 3,644,457, 1 mol of a diphenylmethane diisocyanate is reacted with from about 0.1 to about 0.3 mols of poly-1,2-propylene ether glycol. While the products made according to this patent have met with commercial success, they still suffer from a serious drawback. Specifically, it has been found that these adducts generally will crystallize anywhere from 5° C. to as high as 25° C. In fact, when supplied in commercial quantities, these adducts are generally transported in heated trucks. Addditionally, in order to thaw the materials, it is generally necessary to heat them to somewhere in excess of 50° to 60° C. While in warmer climates, there may not be any problem, in colder areas where the product may be stored in tanks over a period of time, this tendency to crystallize can become a very serious problem. Similar attempts to form liquid diphenylmethane diisocyanates have been described for example, in U.S. Pat. Nos. 3,384,653 and 3,394,164. The attempts to liquify in both of these instances were based on the addition of, in one case, a trihydrocarbyl phosphate, and, in the other case, small amounts of phosphoric acid. In any event, the storage stability of both of these types of products is again quite good around room temperature, but as the temperature decreases, both types of materials tend to crystallize.

It is therefore an object of this invention to provide improved liquid organic diisocyanates which are liquid and stable at temperatures lower than room temperature. A further object of this invention is to provide organic diisocyanates which remain liquid even on prolonged storage at low temperatures.

DESCRIPTION OF THE INVENTION

The instant invention is therefore directed to novel diisocyanate compounds which are both stable and liquid at −5° C. for at least 48 hours which diisocyanate compound comprises the reaction product of a diphenylmethane diisocyanate containing at least 15% by weight of the 2,4'-isomer with either propylene glycol or a poly-1,2-propylene ether glycol. The materials are reacted in an NCO/OH ratio of from about 3:1 to about 15:1, preferably from about 3:1 to about 10:1 and most preferably from about 3:1 to about 6:1. It has been found that when the most preferable NCO/OH ratio is used, novel diisocyanate compounds are obtained which are both stable and liquid at −22° C. for 12 weeks.

The glycol and the isocyanate can be reacted at temperatures ranging anywhere from room temperature (i.e., about 25°) up to 125° C. Preferably, the reaction temperature is from room temperature to about 90° C. and most preferably, from about 40° C. to about 80° C.

In general, the diphenylmethane diisocyanates usable according to the instant invention must contain at least 15 percent by weight of the 2,4'-isomer. While theoretically, there is no upper limit to the amount of 2,4'-isomer which could be present in the isocyanate, as a practical matter, due to availability in the present day isocyanate market, it is generally not possible to have the 2,4'-isomer content in excess of 70 percent. Thus, as a practical rule, the diphenylmethane diisocyanates used according to the instant invention will contain from about 15 to about 70 percent by weight of the 2,4'-isomer with the balance being the 4,4'-isomer and 2,2'-isomer and/or various MDI dimers (the 2,2'-isomer and any dimer are generally present only in trace amounts, i.e., less than 1 percent by weight). Preferably, the 2,4'-isomer content is from about 20 to about 65 percent by weight and most preferably from about 40 to about 65 percent by weight.

The liquid diisocyanates which can be prepared according to the instant invention have a relatively low viscosity and can therefore be worked up very easily, e.g., they can be cast or metered through pumps. In addition, they have a very low vapor pressure and are therefore substantially physiologically harmless. Since the reaction can generally be carried out at relatively low temperatures, the diisocyanate structure of the product of the process is completely preserved. Allophanate formation by the reaction of the resulting urethane groups with the isocyanate group to produce a polyisocyanate apparently does not take place to any large degree. This is true even when forming the reaction product at a temperature of 125° C.

In addition to propylene glycol, the poly-1,2-propylene ether glycols usable in the instant invention include essentially any ranging from a molecular weight of 134 (i.e. dipropylene glycol) up to molecular weights of about 2000. Specific examples include dipropylene glycol, tripropylene glycols, and various polypropylene glycols.

The process of the instant invention may be carried out by introducing the glycols into the diisocyanate at temperatures of from room temperature up to about 125° C. with stirring. Alternatively, the diisocyanate can be introduced into the glycols. The isocyanate content of the products of the process generally amounts to from as low as about 10 percent to as high as about 30 percent.

The products of the process can be used for all types of different polyaddition reactions in the lacquer and plastics industries, e.g. for the production of polyurethane foams or polyurethane elastomers which are in turn useful for the preparation of cushions or gear wheels respectively. Because of their low freezing point, the materials can be transported and stored at reasonably cold temperatures. In fact, it will be clear from the examples which follow, many of the products of the instant invention do not freeze when stored at −22° C. for 12 weeks. Yet a further advantage of the reaction products of the instant invention resides in the fact that even if the products should freeze, they will readily thaw at room temperature. This is completely different from the materials disclosed in U.S. Pat. No. 3,644,457, which upon freezing, must be heated to in excess of 50° C.

The invention is further illustrated by the following examples in which all parts are by weight unless otherwise specified.

EXAMPLES

EXAMPLES 1 THROUGH 8

In these eight examples, the diphenylmethane diisocyanate, having the isomer ratio specified in Table I were charged to a reactor and heated to 50° C. Tripropylene glycol was then added at such a rate that the temperature did not exceed 60° C. (in some instances, cooling was required). The amount of tripropylene glycol added was such that the NCO/OH ratio was about 4.9 in each instance. After all the tripropylene glycol was added, the reaction mixture was maintained at 60° C. for about three hours. Samples were then analyzed for viscosity and NCO content and then stored in a freezer for 48 hours at −5° C. After the 48 hours storage, the samples were removed from the freezer. Results are set forth in Table I.

TABLE I

| Ex. No. | Isomer Ratio 4,4'/2,4' | NCO/OH Ratio | % NCO by Wt. | Viscosity cps at 25° C | Storage Stability After 48 Hours at −5° C |
|---|---|---|---|---|---|
| 1 | 100/0 | 4.9 | 22.7 | 604 | Completely Solid |
| 2 | 92/8 | 4.9 | 23.1 | 656 | Completely Solid |
| 3 | 84/16 | 4.9 | 22.8 | 664 | Liquid* |
| 4 | 76/24 | 4.9 | 22.8 | 695 | Liquid |
| 5 | 68/32 | 4.9 | 22.6 | 840 | Liquid |
| 6 | 60/40 | 4.9 | 22.5 | 850 | Liquid |
| 7 | 43/57 | 4.9 | 22.8 | 720 | Liquid |
| 8 | 35/65 | 4.9 | 22.8 | 690 | Liquid |

*After an additional 24 hours at −5° C, traces of crystals could be observed, but the product was still liquid.

In order to establish the outstanding storage stability at even lower temperatures, the products of Examples 6, 7 and 8 were stored in a freezer for 12 (twelve) weeks at −22° C. After this period of time, none of the products crystallized.

After bringing the products back to room temperature, viscosities and % NCO were rechecked and found to be unchanged.

EXAMPLES 9 THROUGH 12

The process of Examples 1 through 8 was followed except that NCO/OH ratios were varied as set forth in Table II while the isomer ratio was kept constant. Tripropylene glycol was again used. Results are set forth in Table II.

After bringing the products back to room temperature, viscosities and % NCO were rechecked and found to be unchanged.

TABLE II

| Ex. No. | Isomer Ratio 4,4'/2,4' | NCO/OH Ratio | % NCO By Wt. | Viscosity cps at 25° C | Storage Stability After 48 Hours at −5° C |
|---|---|---|---|---|---|
| 9 | 35/65 | 3.3 | 18.8 | 10,050 | Liquid |
| 10 | 35/65 | 4.9 | 22.8 | 690 | Liquid |
| 11 | 35/65 | 10.0 | 28.1 | 70 | Liquid |
| 12 | 35/65 | 15.0 | 29.7 | 35 | Liquid |

The products of Examples 9 through 12 were then stored in a freezer for 12 weeks at −22° C. After this period of time, the products of Examples 9 and 10 remained liquid while the products of Examples 11 and 12 had crystallized.

EXAMPLES 13 THROUGH 17

The process of Examples 9 through 12 was followed using an NCO/OH ratio of about 4.9, but using various reaction temperatures, and heated for the time specified in Table III. The temperature times of reaction and results were as set forth in Table III.

TABLE III

| Example No. | Isomer Ratio 4,4'/2,4' | Reaction Temp. &/Time Hr. | % NCO By Wt. | Viscosity cps at 25° C | Storage Stability After 48 Hours at −5° C |
|---|---|---|---|---|---|
| 13 | 35/65 | Rt (25° C)/14 Hr. | 23.2 | 760 | Liquid |
| 14 | 35/65 | 50 °/8 Hr. | 23.1 | 700 | Liquid |
| 15 | 35/65 | 60°/3 Hr. | 22.8 | 690 | Liquid |
| 16 | 35/65 | 100°/1 Hr. | 22.9 | 840 | Liquid |
| 17 | 35/65 | 120°/0.5 Hr. | 22.8 | 960 | Liquid |

After storage in a freezer for 12 (twelve) weeks at −22° C., none of the products had crystallized.

EXAMPLES 18 THROUGH 27

The process of Examples 1 through 8 was repeated using various NCO/OH ratios, various propylene glycols and an isomer ratio of 35/65 (4,4'/2,4'). The variables were as set forth in Table IV.

TABLE IV

| Ex. No. | Glycol Used | NCO/OH Ratio | % NCO By Wt. | Viscosity cps at 25° C | Storage Stability After 48 Hours at −5° C |
|---|---|---|---|---|---|
| 18 | 1,2-Propylene Glycol MW 76 | 4.9 | 24.8 | 710 | Liquid |
| 19 | Dipropylene Glycol MW 134 | 4.9 | 23.9 | 810 | Liquid |
| 20 | Tripropylene Glycol MW 192 | 4.9 | 22.9 | 690 | Liquid |
| 21 | Polypropylene Glycol Avg. MW 150 | 4.9 | 23.7 | 655 | Liquid |
| 22 | Polypropylene Glycol Avg. MW 446 | 4.9 | 20.0 | 920 | Liquid |
| 23 | Polypropylene Glycol Avg. MW 100 | 4.9 | 14.7 | 2080 | Liquid |
| 24 | Polypropylene Glycol Avg. MW 2000 | 4.9 | 10.0 | 3260 | Liquid |
| 25 | Polypropylene Glycol Avg. MW 1000 | 10 | 21.6 | 190 | Liquid |
| 26 | Polypropylene Glycol Avg. MW 2000 | 10 | 16.7 | 500 | Liquid |
| 27 | Polypropylene Glycol Avg. MW 2000 | 15 | 20.4 | 190 | Liquid |

The products of Examples 18 through 22, 25, 26 and 27 were then stored in a freezer for twelve (12) weeks at −22° C. After this period of time, the products of Examples 18 through 22 remained liquid, while the products of Examples 25, 26 and 27 had crystallized.

It is to be understood that the foregoing examples are given for the purpose of illustration and that various other materials within the definition of the claims could be used. Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate compound which is both stable and liquid at −5° C. for at least 48 hours, comprising the reaction product of:
    (a) a diphenylmethane diisocyanate containing from about 15 to about 70 percent by weight of the 2,4'-isomer, and
    (b) a material selected from the group consisting of propylene glycol and poly-1,2-propylene ether glycols.
2. The compound of claim 1 wherein the balance of said diphenylmethane diisocyanate is the 4,4'-isomer.
3. The compound of claim 2, wherein said diphenylmethane diisocyanate comprises:
    (a) from about 20 to about 65 percent by weight of the 2,4'-isomer, and the balance being
    (b) the 4,4'-isomer.
4. The compound of claim 3, wherein said diphenylmethane diisocyanate comprises:
    (a) from about 40 to about 65 percent by weight of the 2,4'-isomer, and the balance being
    (b) the 4,4'-isomer.
5. The compound of claim 2, wherein components (a) and (b) are used in such quantities that the NCO/OH ratio is from about 3:1 to about 15:1.
6. The compound of claim 5, wherein said ratio is from about 3:1 to about 10:1.
7. The compound of claim 6, wherein said ratio is from about 3:1 to about 6:1.
8. The compound of claim 2, wherein said poly-1,2-propylene ether glycols have molecular weights of from 134 to about 2000.
9. The compound of claim 1, wherein components (a) and (b) are used in such quantities that the NCO/OH ratio is from about 3:1 to about 15:1.
10. The compound of claim 9, wherein said ratio is from about 3:1 to about 10:1.
11. The compound of claim 10, wherein said diphenylmethane diisocyanate comprises:
    (a) from about 20 to about 65 percent by weight of the 2,4'-isomer, and the balance being
    (b) the 4,4'-isomer.
12. The compound of claim 10, wherein said ratio is from about 3:1 to about 6:1.
13. The compound of claim 12, wherein said diphenylmethane diisocyanate comprises:
    (a) from about 40 to about 65 percent by weight of the 2,4'-isomer, and the balance being
    (b) the 4,4'-isomer.
14. The compound of claim 12, wherein said poly-1,2-propylene ether glycols have molecular weights of from 134 to about 2000.
15. The compound of claim 9, wherein said poly-1,2-propylene ether glycols have molecular weights of from 134 to about 2000.
16. A process for the production of diisocyanate compounds which are both stable and liquid at −5° C. for at least 48 hours which comprises reacting:
    (a) a diphenylmethane diisocyanate containing from about 15 to about 70 percent by weight of the 2,4'-isomer, and
    (b) a material selected from the group consisting of propylene glycol and poly-1,2-propylene ether glycols.
17. The process of claim 16, wherein said components (a) and (b) are reacted at a temperature of from room temperature to about 125° C.
18. The process of claim 17, wherein the balance of said diphenylmethane diisocyanate the 4,4'-isomer.
19. The process of claim 18, wherein components (a) and (b) are used in such quantities that the NCO/OH ratio is from about 3:1 to about 15:1.
20. The process of claim 19, wherein said poly-1,2-propylene ether glycols have molecular weights of from 134 to about 2000.
21. The process of claim 20, wherein said components (a) and (b) are reacted at a temperature of from room temperature to about 90° C.
22. The process of claim 21, wherein said components (a) and (b) are reacted at a temperature of from about 40° C. to about 80° C.

* * * * *